(12) United States Patent
Hsieh

(10) Patent No.: US 6,654,442 B2
(45) Date of Patent: Nov. 25, 2003

(54) METHODS AND APPARATUS FOR WEIGHTING PROJECTION DATA

(75) Inventor: Jiang Hsieh, Brookfield, WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 10/113,532

(22) Filed: Mar. 29, 2002

(65) Prior Publication Data

US 2003/0185337 A1 Oct. 2, 2003

(51) Int. Cl.$^7$ .................................................. A61B 6/03
(52) U.S. Cl. ................................. 378/15; 378/4; 378/94
(58) Field of Search ............................ 378/4, 8, 15, 901

(56) References Cited

U.S. PATENT DOCUMENTS

| | | |
|---|---|---|
| 5,416,815 A | 5/1995 | Hsieh |
| 5,515,409 A | 5/1996 | Hsieh |
| 5,610,964 A | 3/1997 | Flohr et al. |
| 5,727,041 A | 3/1998 | Hsieh |
| 5,812,628 A | 9/1998 | Hsieh |
| 6,035,012 A | 3/2000 | Hsieh |
| 6,061,419 A | 5/2000 | Hsieh et al. |
| 6,061,420 A | 5/2000 | Strong et al. |
| 6,115,487 A | 9/2000 | Toth et al. |
| 6,134,292 A | 10/2000 | Hsieh |
| 6,215,841 B1 | 4/2001 | Hsieh |
| 6,233,308 B1 | 5/2001 | Hsieh |
| 6,339,632 B1 | 1/2002 | Besson |
| 6,418,184 B1 * | 7/2002 | Wang et al. .................. 378/15 |
| 6,421,411 B1 | 7/2002 | Hsieh |

\* cited by examiner

Primary Examiner—David V. Bruce
(74) Attorney, Agent, or Firm—Carl B. Horton, Esq.; Armstrong Teasdale LLP

(57) ABSTRACT

A method for weighting projection data includes selecting a region that includes a plurality of projection data samples, dividing the region into a plurality of equally sized sub-regions, and weighting the equally sized sub-regions using a location dependent z-smoothing weighting function.

20 Claims, 5 Drawing Sheets

METHODS AND APPARATUS FOR WEIGHTING PROJECTION DATA

BACKGROUND OF THE INVENTION

This invention relates to computed tomographic (CT) imaging, and more particularly to methods and apparatus for weighting projection data acquired using a multi-slice CT imaging system.

For some known multi-slice helical scans, reconstructed with a fan-beam based algorithm, there is an error due to a cone beam effect of a projection sampling. The error in a reconstructed image increases with an increase of a distance of an image pixel to a system iso-center. Therefore, for pixels located near the system iso-center, a plurality of projection rays are near a reconstructed pixel location and an amount of cone beam error is relatively small. For pixels that are located further away from the system iso-center, a difference between the location where the projection sample passes and the location of the backprojected pixel is large and the amount of cone-beam error is relatively large.

BRIEF DESCRIPTION OF THE INVENTION

In one aspect, a method for weighting projection data is provided. The method includes selecting a region that includes a plurality of projection data samples, dividing the region into a plurality of equally sized sub-regions, and weighting the equally sized sub-regions using a location dependent z-smoothing weighting function.

In another aspect, a computer for weighting projection data acquired using a medical imaging system is provided. The imaging system includes a radiation source and a detector. The computer is programmed to select a region that includes a plurality of projection data samples, divide the region into a plurality of equally sized sub-regions, and weight the equally sized sub-regions using a location dependent z-smoothing weighting function.

In a further aspect, a computed tomographic (CT) imaging system for weighting projection data is provided. The CT system includes a radiation source, a detector array, and a computer coupled to the detector array and the radiation source and configured to select a region that includes a plurality of projection data samples, divide the region into a plurality of equally sized sub-regions, and weight the equally sized sub-regions using a location dependent z-smoothing weighting function.

DETAILED DESCRIPTION OF THE INVENTION

Figure 1:
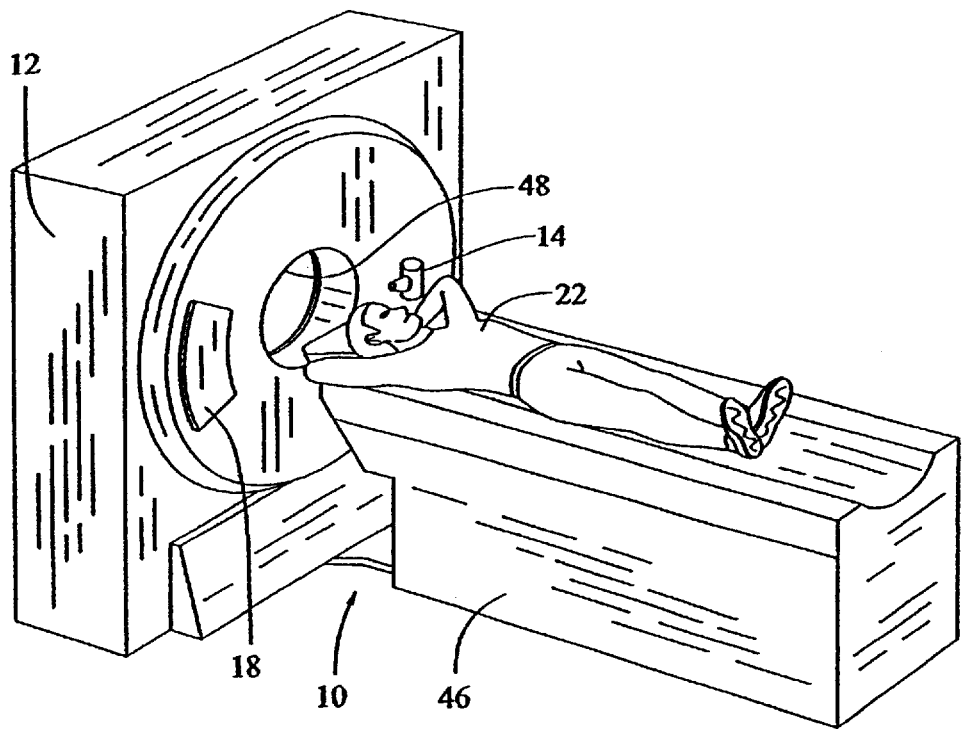
FIG. 1 is a pictorial view of a CT imaging system.

In some known CT imaging system configurations, an x-ray source projects a fan-shaped beam which is collimated to lie within an X-Y plane of a Cartesian coordinate system and generally referred to as an "imaging plane". The x-ray beam passes through an object being imaged, such as a patient. The beam, after being attenuated by the object, impinges upon an array of radiation detectors. The intensity of the attenuated radiation beam received at the detector array is dependent upon the attenuation of an x-ray beam by the object. Each detector element of the array produces a separate electrical signal that is a measurement of the beam attenuation at the detector location. The attenuation measurements from all the detectors are acquired separately to produce a transmission profile.

In third generation CT systems, the x-ray source and the detector array are rotated with a gantry within the imaging plane and around the object to be imaged such that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles, or view angles, during one revolution of the x-ray source and detector.

In an axial scan, the projection data is processed to construct an image that corresponds to a two dimensional slice taken through the object. One method for reconstructing an image from a set of projection data is referred to in the art as the filtered back projection technique. This process converts the attenuation measurements from a scan into integers called "CT numbers" or "Hounsfield units", which are used to control the brightness of a corresponding pixel on a cathode ray tube display.

To reduce the total scan time, a "helical" scan may be performed. To perform a "helical" scan, the patient is moved while the data for the prescribed number of slices is acquired. Such a system generates a single helix from a fan beam helical scan for a single slice CT. For multi-slice CT, multiple helixes are generated from a fan beam helical scan. The helix mapped out by the fan beam yields projection data from which images in each prescribed slice may be reconstructed.

Reconstruction algorithms for helical scanning typically use helical weighing algorithms that weight the collected data as a function of view angle and detector channel index. Specifically, prior to a filtered back projection process, the data is weighted according to a helical weighing factor, which is a function of both the gantry angle and detector angle. The weighted data is then processed to generate CT numbers and to construct an image that corresponds to a two dimensional slice taken through the object.

As used herein, an element or step recited in the singular and preceded with the word "a" or "an" should be understood as not excluding plural said elements or steps, unless such exclusion is explicitly recited. Furthermore, references to "one embodiment" of the present invention are not intended to be interpreted as excluding the existence of additional embodiments that also incorporate the recited features.

Also as used herein, the phrase "reconstructing an image" is not intended to exclude embodiments of the present invention in which data representing an image is generated but a viewable image is not. However, many embodiments generate (or are configured to generate) at least one viewable image.

Figure 2:
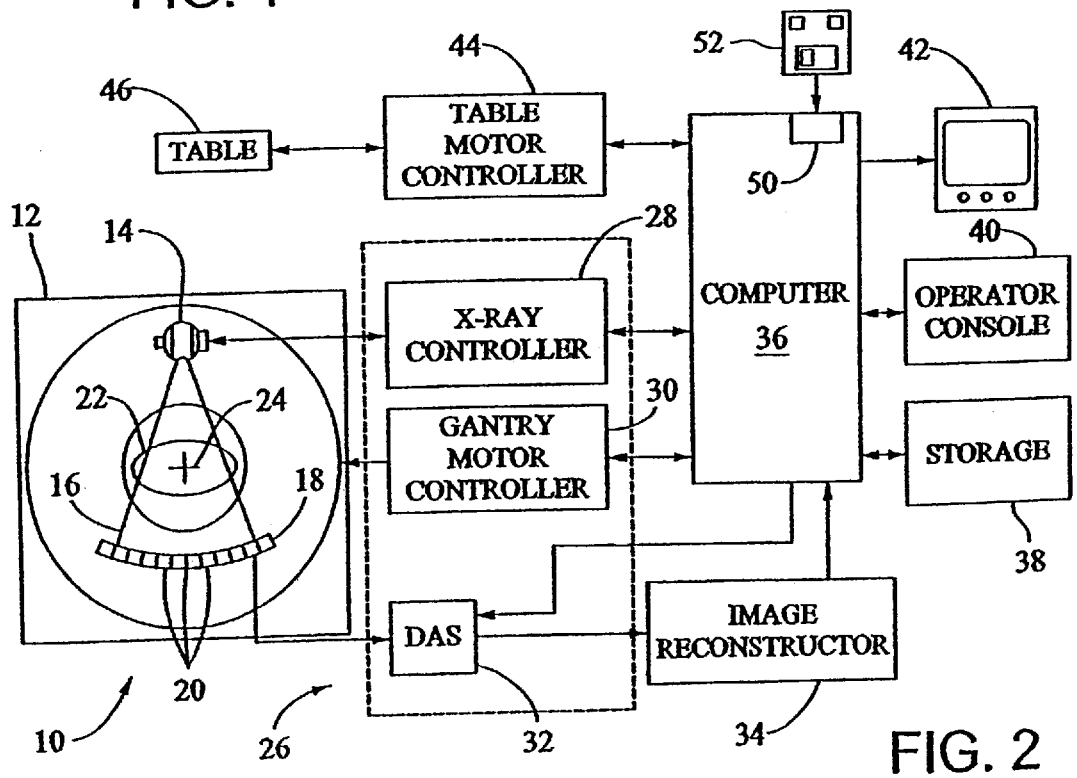
FIG. 2 is a block schematic diagram of the system illustrated in FIG. 1.

Referring to FIGS. 1 and 2, a multi-slice scanning imaging system, for example, computed tomography (CT) imaging system 10, is shown as including a gantry 12 representative of a "third generation" CT imaging system. Gantry 12 has an x-ray source 14 that projects a beam of x-rays 16 toward a detector array 18 on the opposite side of gantry 12. Detector array 18 is formed by a plurality of detector rows (not shown) including a plurality of detector elements 20 which together sense the projected x-rays that pass through an object, such as a medical patient 22. Each detector element 20 produces an electrical signal that represents the intensity of an impinging x-ray beam and hence the attenuation of the beam as it passes through object or patient 22. During a scan to acquire x-ray projection data, gantry 12 and the components mounted thereon rotate about a center of rotation 24. FIG. 2 shows only a single, row of detector elements 20 (i.e., a detector row). However, multislice detector array 18 includes a plurality of parallel detector rows of detector elements 20 so that projection data corresponding to a plurality of quasi-parallel or parallel slices can be acquired simultaneously during a scan.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high-speed image reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 in gantry 12. Particularly, table 46 moves portions of patient 22 through gantry opening 48.

In one embodiment, computer 36 includes a device 50, for example, a floppy disk drive or CD-ROM drive, for reading instructions and/or data from a computer-readable medium 52, such as a floppy disk or CD-ROM. In another embodiment, computer 36 executes instructions stored in firmware (not shown). Computer 36 is programmed to perform functions described herein, accordingly, as used herein, the term computer is not limited to just those integrated circuits referred to in the art as computers, but broadly refers to computers, processors, microcontrollers, microcomputers, programmable logic controllers, application specific integrated circuits, and other programmable circuits.

Figure 3:
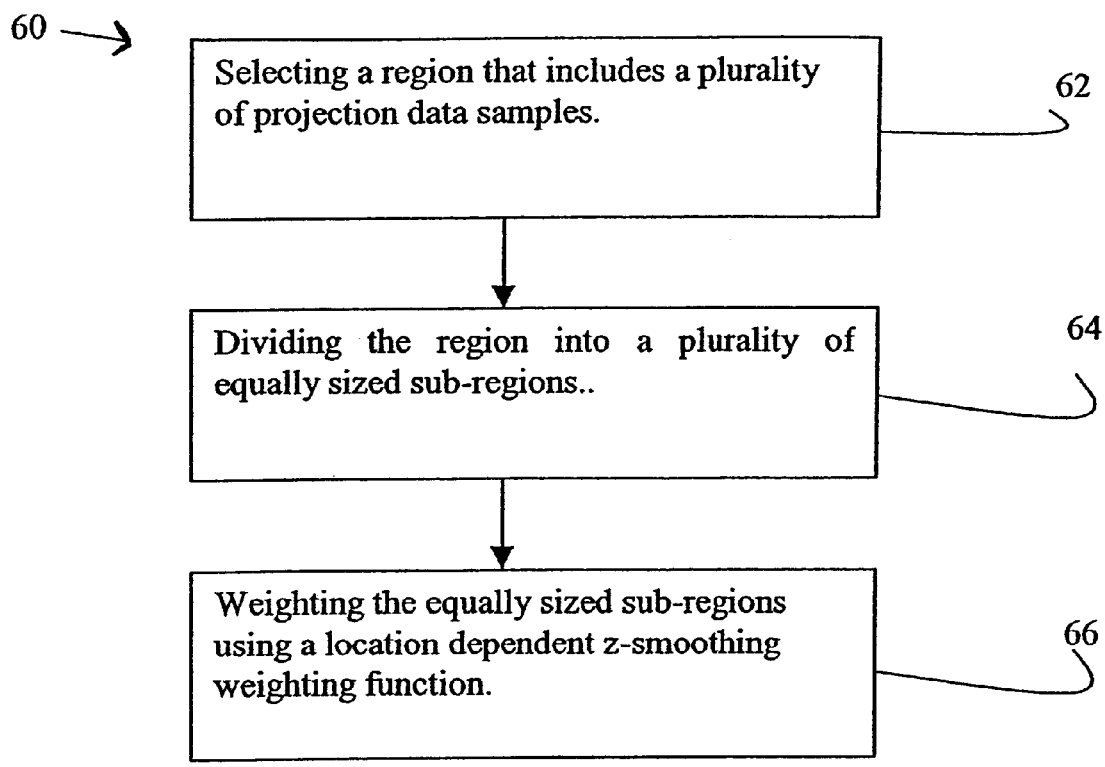
FIG. 3 is a flow diagram of a method for weighting projection data.

FIG. 3 is a flow diagram of a method 60 for weighting projection data. Method 60 includes selecting 62 a region that includes a plurality of projection data samples, dividing 64 the region into a plurality of equally sized sub-regions, and weighting 66 the equally sized sub-regions using a location dependent z-smoothing weighting function.

Figure 4:
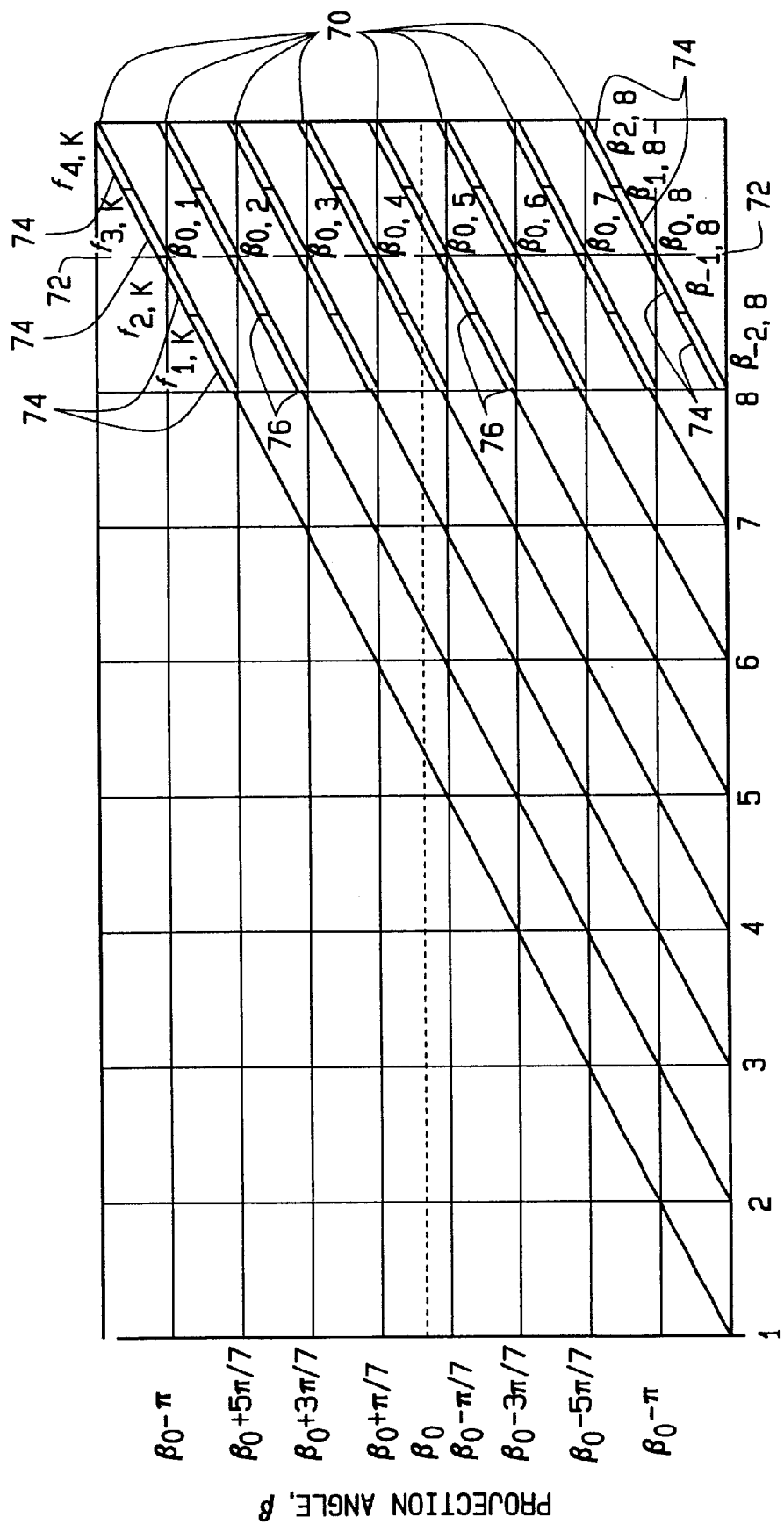
FIG. 4 is detector sampling pattern as a function of detector location and projection angle.

FIG. 4 is a sampling pattern for a plurality of iso-rays of a multi-slice CT. In the exemplary embodiment, the loci of detector 18 (shown in FIG. 1) iso-channels are plotted as functions of both a projection angle $\beta$, and detector 18 location on a z axis, to generate a plurality of diagonal lines as shown in FIG. 4. Detector 18 includes M rows and scans at an N:1 helical pitch to generate a plurality of projection data. In the exemplary embodiment, detector 18 includes eight rows, i.e. M=8, and scans at a 7:1 helical pitch.

Selecting 62 a region 70 that includes a plurality of projection data samples includes selecting a plurality of projection data samples that are within $2\pi/N$ in projection angle $\beta$ on either side of a plane of reconstruction (POR) 72. In another embodiment, a size of region 70 is selected based on a desired smoothing. POR 72 is defined as a straight line in sinogram space that intersects each row k at:

$$\beta_k = \beta_{0,k} - \gamma \qquad \text{Equation 1}$$

where:

$\beta_{0,k}$ is a projection angle at which the iso-channel of detector row k intersects the plane of reconstruction; and $\gamma$ is a detector angle.

Dividing 64 region 70 into a plurality of equally sized sub-regions 74 includes dividing region 70 of each detector row into four sub-regions 74, wherein each sub-region 74 covers a projection angle $\beta$ range of approximately $\pi/N$, as shown in FIG. 4. In another embodiment, a region 70 greater than $2\pi/N$ in projection angle $\beta$ can be selected and then divided into greater than four sub-regions 74.

Each sub-region 74 includes two boundaries ($\beta_{n,k}$) 76 which are defined in accordance with $$\beta_{n,k} = \beta_0 + \frac{(2k - M - 1 + n)\pi}{N}, \qquad \text{Equation 2}$$

where:

n=−2, −1, 0, 1, and 2; and k=1, ... ,M. and wherein $\beta_0$ is a projection angle of a center view, k is a detector row index, M is the number of detector rows, n is a sub-region index, and N is a helical pitch.

In the exemplary embodiment, all regions 70 in sinogram space which are conjugate include the same shape and are bounded by $\beta_{n,k}-\gamma$ lines. In one embodiment, weighting 66 sub-regions 74 using a location dependent z-smoothing weighting function $w_k(\gamma,\beta)$ includes selecting the weighting function that satisfies two conditions. The weighting function, $w_k(\gamma,\beta)$ function is an even function of fan angle $\gamma$ parallel to the sub-region boundaries, and the weighting function, $w_k(\gamma,\beta)$ preserves a summation unity. In one embodiment, the weighting function $w_k(\gamma,\beta)$ is represented by separate functions in each sub-region 74 according to $$w_k(\gamma,\beta) = f_{n,k}(\gamma,\beta), \text{ for } \beta_{n,k}-\gamma \leq \beta \leq \beta_{n+1,k}-\gamma$$

where $f_{n,k}(\gamma, \beta)$ is a weighting function for a sub-region 74, $\gamma$ is a fan angle, $\beta$ is a projection angle, n is an index for sub-regions, and k is a detector row index.

The two conditions described previously herein can be represented by the following equations $$w_k(\gamma,\beta) = w_k(-\gamma,\beta-\gamma), \qquad \text{Equation 4}$$

$$\sum_{n=1}^{4} f_{n,k}(\gamma, \Delta\beta + \beta_{n,k} - \gamma) = 1 \text{ for } 0 \le \Delta\beta < \frac{\pi}{N} \quad \text{Equation 5}$$

where n is an index for sub-regions, and k is the index for detector rows.

In one embodiment, the weighting function, for detector rows k=1 . . . 4, is defined as:

$f_{1,k}(\gamma,\beta-\beta_{1,k})=\alpha(\gamma)\eta_1(\beta)/[1+2\alpha(\gamma)]$    Equation 6

$f_{2,k}(\gamma,\beta-\beta_{2,k})=\{[1-\alpha(\gamma)]\eta_2(\beta)+\alpha(\gamma)\}/[1+2\alpha(\gamma)]$    Equation 7

$f_{3,k}(\gamma,\beta-\beta_{3,k})=\{1-[1-\alpha(\gamma)]\eta_2(\beta)\}/[1+2\alpha(\gamma)]$    Equation 8

$f_{4,k}(\gamma,\beta-\beta_{4,k})=\alpha(\gamma)[1-\eta_2(\beta)]/[1+2\alpha(\gamma)]$    Equation 9 where $$\alpha(\gamma) = \frac{|\gamma| + \gamma_b}{2(\gamma_m + \gamma_b)}, \quad \text{Equation 10}$$

$$\eta_n(\beta) = \frac{\lfloor \beta - (\beta_{n,k} - \gamma) \rfloor N}{\pi}, \quad \text{Equation 11}$$

$\gamma_b$ ($0 \le \gamma_b < \infty$) is a parameter to adjust the variation of the weighting function from the central channels to the boundary channels, and $\gamma_m$ is the maximum detector angle in $\gamma$.

In one embodiment, $\Gamma_b$ is set to 0.48. When $\gamma_b$, approaches infinity, the weighting function is uniform across all channels.

Figure 5:
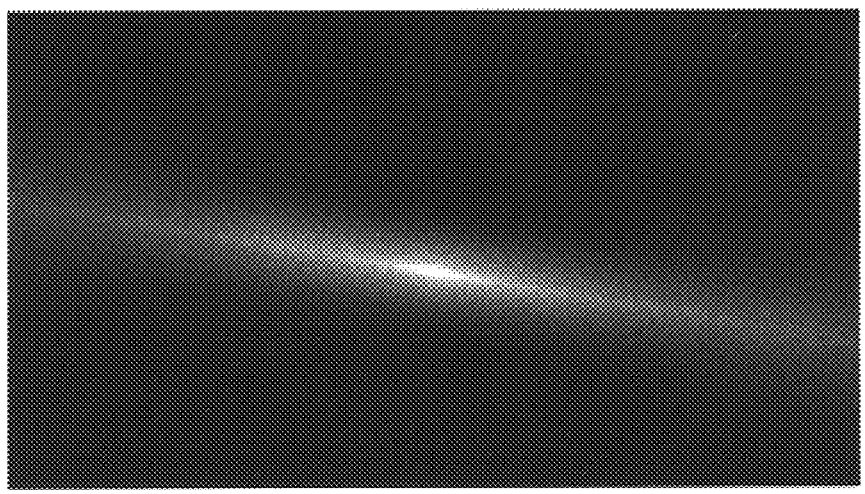
FIG. 5 is an image of a weighting function for one of the detector rows
Figure 6:
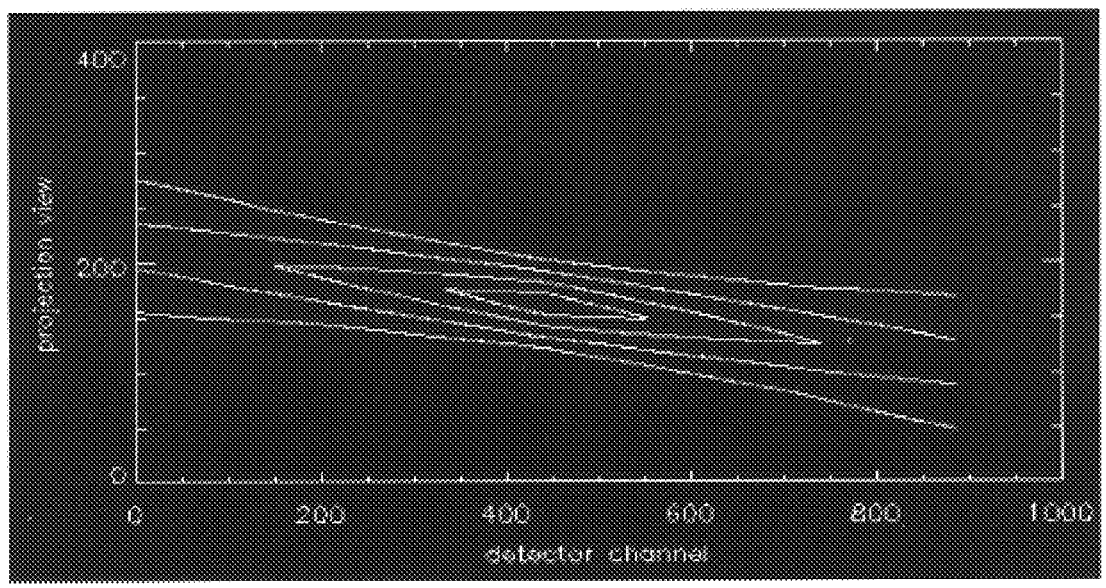
FIG. 6 is a contour plot of the weighting function shown in FIG. 5.

FIG. 5 is an image of a weighting function for one of the rows in an eight-row detector. FIG. 6 is a contour plot of the weighting function shown in FIG. 5 which illustrates the weighting function of one of the detector rows (all rows have identical weighting function except a shift in $\beta$) over a sub-set of view angles in which the weighting function is non-zero.

Figure 7:
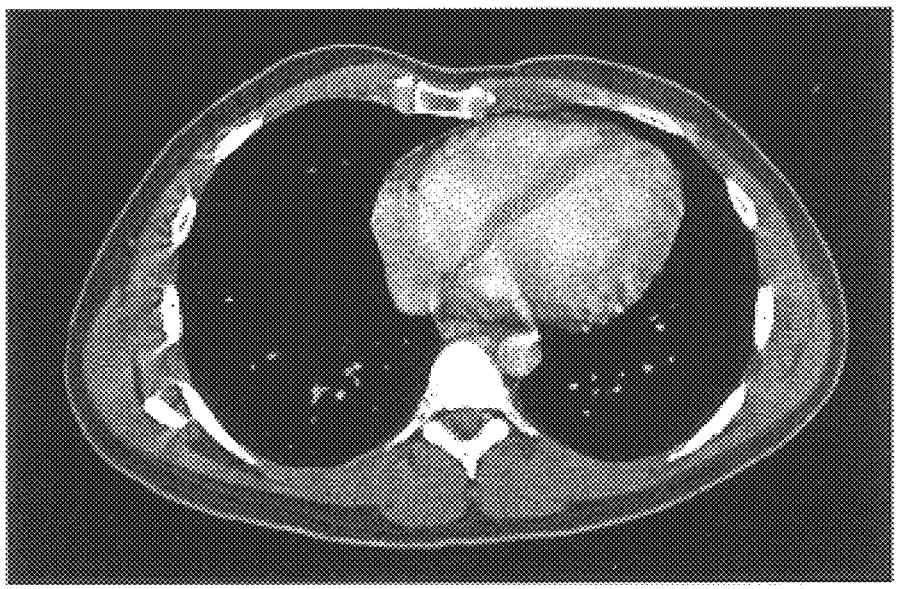
FIG. 7 is a scan reconstructed with a known reconstruction algorithm.
Figure 8:
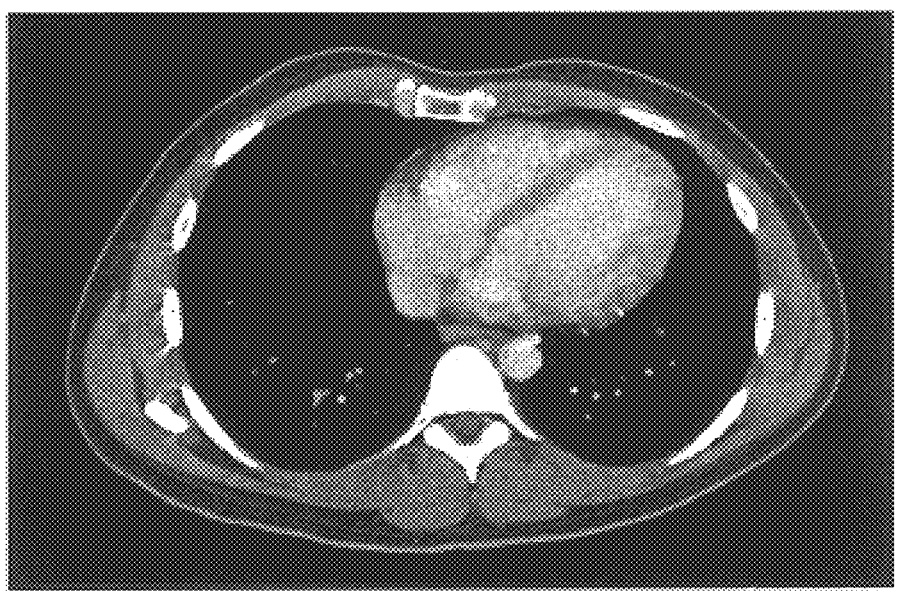
FIG. 8 is a scan reconstructed with a proposed reconstruction algorithm.

FIG. 7 is a scan reconstructed with a known reconstruction algorithm. FIG. 8 is a scan reconstructed with the algorithm described herein. The algorithm was applied to a patient scan with known helical interpolation and cone beam image artifacts. The scan was reconstructed with both the original reconstruction algorithm as shown in FIG. 7 and the location dependent z-smoothing weighting function as shown in FIG. 8. Improvement in image quality is apparent. Streaking artifacts near the ribs are nearly completely eliminated.

The projection space technique described herein, using the projection weighting function to perform location dependent z-smoothing facilitates reduced computation, since no separate processing is required. In addition, images can be generated at any locations without the constraints that they need to be adjacent to each other to enable image filtering.

While the invention has been described in terms of various specific embodiments, those skilled in the art will recognize that the invention can be practiced with modification within the spirit and scope of the claims.

What is claimed is:

1. A method for weighting projection data, said method comprising:

selecting a region that includes a plurality of projection data samples;

dividing the region into a plurality of equally sized sub-regions; and weighting the equally sized sub-regions using a location dependent z-smoothing weighting function.

2. A method in accordance with claim 1 wherein selecting a region that includes a plurality of projection data samples comprises selecting a region that includes a plurality of projection data samples that are within $2\pi/N$ in projection angle $\beta$ on either side of a plane of reconstruction.

3. A method in accordance with claim 1 further comprising defining a boundary of the sub-regions in accordance with:

$$\beta_{n,k} = \beta_0 + \frac{(2k - M - 1 + n)\pi}{N};$$

where:

n=−2, −1, 0, 1, and 2; and k=1, . . . ,M.; and wherein:

$\beta_0$ is a projection angle of a center view;

k is a single detector row;

M is a number of detector rows;

n is a sub-region index; and

N is a helical pitch.

4. A method in accordance with claim 1 further comprising selecting a weighting function that is an even function of a fan angle $\gamma$, parallel to the sub-regions and a summation of the weighting is unity.

5. A method in accordance with claim 4 wherein selecting a weighting function comprises selecting a weighting function in accordance with:

$w_k(\gamma,\beta)=w_k(-\gamma,\beta-\gamma)$ $$\sum_{n=1}^{4} f_{n,k}(\gamma, \Delta\beta + \beta_{n,k} - \gamma) = 1 \text{ for } 0 \le \Delta\beta < \frac{\pi}{N}$$

where:

$\gamma$ is a fan angle;

$\beta$ is a projection angle change;

n is an index for sub-regions; and k is the index for detector rows.

6. A method in accordance with claim 1 wherein weighting the equally sized sub-regions using a location dependent z-smoothing weighting function comprises weighting the equally sized sub-regions using a location dependent z-smoothing weighting function in accordance with:

$f_{1,k}(\gamma,\beta-\beta_{1,k})=\alpha(\gamma)\eta_1(\beta)/[1+2\alpha(\gamma)]$ $f_{2,k}(\gamma,\beta-\beta_{2,k})=\{[1-\alpha(\gamma)]\eta_2(\beta)+\alpha(\gamma)\}/[1+2\alpha(\gamma)]$ $f_{3,k}(\gamma,\beta-\beta_{3,k})=\{1-[1-\alpha(\gamma)]\eta_2(\beta)\}/[1+2\alpha(\gamma)]$ $f_{4,k}(\gamma,\beta-\beta_{4,k})=\alpha(\gamma)[1-\eta_2(\beta)]/[1+2\alpha(\gamma)]$ where:

$\beta$ is a projection angle;

$\beta_{n,k}$ is a sub-region boundary;

$\gamma$ is a fan angle;

$$\alpha(\gamma) = \frac{|\gamma| + \gamma_b}{2(\gamma_m + \gamma_b)};$$

-continued $$\eta_n(\beta) = \frac{\lfloor \beta - (\beta_{n,k} - \gamma) \rfloor N}{\pi};$$

$\gamma_b (0 \leq \gamma_b < \infty)$ is a parameter to adjust the variation of the weighting function from the central channels to the boundary channels; and $\gamma_m$ is the maximum detector angle in $\gamma$.

7. A method for weighting projection data, said method comprising:

selecting a region that includes a plurality of projection data samples that are within $2\pi/N$ in projection angle $\beta$ on either side of a plane of reconstruction;

dividing the region into a plurality of equally sized sub-regions;

defining a boundary of the sub-regions in accordance with:

$$\beta_{n,k} = \beta_0 + \frac{(2k - M - 1 + n)\pi}{N};$$

where:

n=−2, −1, 0, 1, or 2; and k=1, . . . ,M; and wherein:

$\beta_0$ is a projection angle of a center view;

k is a single detector row;

M is a number of detector rows;

n is a sub-region index; and

N is a helical pitch; and weighting the equally sized sub-regions using a location dependent z-smoothing weighting function in accordance with:

$f_{1,k}(\gamma,\beta-\beta_{1,k})=\alpha(\gamma)\eta_1(\beta)/[1+2\alpha(\gamma)]$ $f_{2,k}(\gamma,\beta-\beta_{2,k})=\{[1-\alpha(\gamma)]\eta_2(\beta)+\alpha(\gamma)\}/[1+2\alpha(\gamma)]$ $f_{3,k}(\gamma,\beta-\beta_{3,k})=\{1-[1-\alpha(\gamma)]\eta_2(\beta)\}/[1+2\alpha(\gamma)]$ $f_{4,k}(\gamma,\beta-\beta_{4,k})=\alpha(\gamma)[1-\eta_2(\beta)]/[1+2\alpha(\gamma)]$ where:

$\beta$ is a projection angle;

$\beta_{n,k}$ is a sub-region boundary;

$\gamma$ is a fan angle;

$$\alpha(\gamma) = \frac{|\gamma| + \gamma_b}{2(\gamma_m + \gamma_b)};$$

$$\eta_n(\beta) = \frac{\lfloor \beta - (\beta_{n,k} - \gamma) \rfloor N}{\pi};$$

$\gamma_b (0 \leq \gamma_b < \infty)$ is a parameter to adjust the variation of the weighting function from the central channels to the boundary channels; and $\gamma_m$ is the maximum detector angle in $\gamma$.

8. A computer for weighting projection data acquired using a medical imaging system, wherein said imaging system comprises a radiation source and a detector, said computer programmed to:

select a region that includes a plurality of projection data samples;

divide the region into a plurality of equally sized sub-regions; and weight the equally sized sub-regions using a location dependent z-smoothing weighting function.

9. A computer in accordance with claim 8 wherein to select a region that includes a plurality of projection data samples, said computer further programmed to select a region that includes a plurality of projection data samples that are within $2\pi/N$ in projection angle $\beta$ on either side of a plane of reconstruction.

10. A computer in accordance with claim 8, said computer further programmed to define a boundary of the sub-regions in accordance with:

$$\beta_{n,k} = \beta_0 + \frac{(2k - M - 1 + n)\pi}{N};$$

where:

n=−2, −1, 0, 1, and 2; and k=1, . . . ,M.; and wherein:

$\beta_0$ is a projection angle of a center view;

k is a single detector row;

M is a number of detector rows;

n is a sub-region index; and

N is a helical pitch.

11. A computer in accordance with claim 8, said computer further programmed to select a weighting function that is an even function of a fan angle $\gamma$ parallel to the sub-regions and a summation of the weighting is unity.

12. A computer in accordance with claim 11 wherein to select a region that includes a plurality of projection data samples, said computer further programmed to select a weighting function in accordance with:

$w_k(\gamma,\beta)=w_k(-\gamma,\beta-\gamma)$ $$\sum_{n=1}^{4} f_{n,k}(\gamma, \Delta\beta + \beta_{n,k} - \gamma) = 1 \text{ for } 0 \leq \Delta\beta < \frac{\pi}{N}$$

where:

$\gamma$ is a fan angle;

$\beta$ is a projection angle change;

n is an index for sub-regions; and k is the index for detector rows.

13. A computer in accordance with claim 8 wherein to weight the equally sized sub-regions using a location dependent z-smoothing weighting function, said computer further programmed to weight the equally sized sub-regions using a location dependent z-smoothing weighting function in accordance with:

$f_{1,k}(\gamma,\beta-\beta_{1,k})=\alpha(\gamma)\eta_1(\beta)/[1+2\alpha(\gamma)]$ $f_{2,k}(\gamma,\beta-\beta_{2,k})=\{[1-\alpha(\gamma)]\eta_2(\beta)+\alpha(\gamma)\}/[1+2\alpha(\gamma)]$ $f_{3,k}(\gamma,\beta-\beta_{3,k})=\{1-[1-\alpha(\gamma)]\eta_2(\beta)\}/[1+2\alpha(\gamma)]$ $f_{4,k}(\gamma,\beta-\beta_{4,k})=\alpha(\gamma)[1-\eta_2(\beta)]/[1+2\alpha(\gamma)]$ where:

$\beta$ is a projection angle;

$\beta_{n,k}$ is a sub-region boundary;

γ is a fan angle;

$$\alpha(\gamma) = \frac{|\gamma| + \gamma_b}{2(\gamma_m + \gamma_b)};$$

$$\eta_n(\beta) = \frac{\lfloor \beta - (\beta_{n,k} - \gamma) \rfloor N}{\pi};$$

$\gamma_b (0 \leq \gamma_b < \infty)$ is a parameter to adjust the variation of the weighting function from the central channels to the boundary channels; and $\gamma_m$ is the maximum detector angle in γ.

14. A computed tomographic (CT) imaging system for weighting projection data, said CT system comprising:
   a radiation source;
   a detector array; and
   a computer coupled to said detector array and said radiation source and configured to:
      select a region that includes a plurality of projection data samples;
      divide the region into a plurality of equally sized sub-regions; and
      weight the equally sized sub-regions using a location dependent z-smoothing weighting function.

15. A CT system in accordance with 14, said computer further configured to select a region that includes a plurality of projection data samples that are within 2π/N in projection angle β on either side of a plane of reconstruction.

16. A CT system in accordance with 14, said computer further configured to define a boundary of the sub-regions in accordance with:

$$\beta_{n,k} = \beta_0 + \frac{(2k - M - 1 + n)\pi}{N};$$

where:
   n=−2, −1, 0, 1, and 2; and k=1, . . . ,M.; and
wherein:
   $\beta_0$ is a projection angle of a center view;
   k is a single detector row;
   M is a number of detector rows;
   n is a sub-region index; and
   N is a helical pitch.

17. A CT system in accordance with 14, said computer further configured to select a weighting function that is an even function of a fan angle γ parallel to the sub-regions and a summation of the weighting is unity.

18. A CT system in accordance with claim 17 wherein to select a region that includes a plurality of projection data samples, said computer further configured to select a weighting function in accordance with:

$$w_k(\gamma,\beta) = w_k(-\gamma,\beta-\gamma)$$

$$\sum_{n=1}^{4} f_{n,k}(\gamma, \Delta\beta + \beta_{n,k} - \gamma) = 1 \text{ for } 0 \leq \Delta\beta < \frac{\pi}{N}$$

where:
   γ is a fan angle;
   β is a projection angle change;
   n is an index for sub-regions; and
   k is the index for detector rows.

19. A CT system in accordance with claim 14 wherein to weight the equally sized sub-regions using a location dependent z-smoothing weighting function, said computer further configured to weight the equally sized sub-regions using a location dependent z-smoothing weighting function in accordance with:

$$f_{1,k}(\gamma,\beta-\beta_{1,k}) = \alpha(\gamma)\eta_1(\beta)/[1+2\alpha(\gamma)]$$

$$f_{2,k}(\gamma,\beta-\beta_{2,k}) = \{[1-\alpha(\gamma)]\eta_2(\beta)+\alpha(\gamma)\}/[1+2\alpha(\gamma)]$$

$$f_{3,k}(\gamma,\beta-\beta_{3,k}) = \{1-[1-\alpha(\gamma)]\eta_2(\beta)\}/[1+2\alpha(\gamma)]$$

$$f_{4,k}(\gamma,\beta-\beta_{4,k}) = \alpha(\gamma)[1-\eta_2(\beta)]/[1+2\alpha(\gamma)]$$

where:
   β is a projection angle;
   $\beta_{n,k}$ is a sub-region boundary;
   γ is a fan angle;

$$\alpha(\gamma) = \frac{|\gamma| + \gamma_b}{2(\gamma_m + \gamma_b)};$$

$$\eta_n(\beta) = \frac{\lfloor \beta - (\beta_{n,k} - \gamma) \rfloor N}{\pi};$$

$\gamma_b (0 \leq \gamma_b < \infty)$ is a parameter to adjust the variation of the weighting function from the central channels to the boundary channels; and $\gamma_m$ is the maximum detector angle in γ.

20. A computed tomographic (CT) imaging system for weighting projection data, said CT system comprising:
   a radiation source;
   a detector array; and
   a computer coupled to said detector array and said radiation source and configured to:
      select a region that includes a plurality of projection data samples that are within 2π/N in projection angle β on either side of a plane of reconstruction;
      divide the region into a plurality of equally sized sub-regions;
      define a boundary of the sub-regions in accordance with:

$$\beta_{n,k} = \beta_0 + \frac{(2k - M - 1 + n)\pi}{N};$$

where:
         n=−2, −1, 0, 1, and 2; and k=1, . . . ,M; and
      wherein:
         $\beta_0$ is a projection angle of a center view;
         k is a single detector row;
         M is a number of detector rows;
         n is a sub-region index; and
         N is a helical pitch; and
      weight the equally sized sub-regions using a location dependent z-smoothing weighting function in accordance with:

$$f_{1,k}(\gamma,\beta-\beta_{1,k}) = \alpha(\gamma)\eta_1(\beta)/[1+2\alpha(\gamma)]$$

$$f_{2,k}(\gamma,\beta-\beta_{2,k}) = \{[1-\alpha(\gamma)]\eta_2(\beta)+\alpha(\gamma)\}/[1+2\alpha(\gamma)]$$

$$f_{3,k}(\gamma,\beta-\beta_{3,k}) = \{1-[1-\alpha(\gamma)]\eta_2(\beta)\}/[1+2\alpha(\gamma)]$$

$$f_{4,k}(\gamma,\beta-\beta_{4,k}) = \alpha(\gamma)[1-\eta_2(\beta)]/[1+2\alpha(\gamma)]$$

where:
         β is a projection angle;
         $\beta_{n,k}$ is a sub-region boundary;

γ is a fan angle;

$$\alpha(\gamma) = \frac{|\gamma| + \gamma_b}{2(\gamma_m + \gamma_b)};$$

$$\eta_n(\beta) = \frac{\lfloor \beta - (\beta_{n,k} - \gamma) \rfloor N}{\pi};$$

$\gamma_b (0 \leq \gamma_b < \infty)$ is a parameter to adjust the variation of the weighting function from the central channels to the boundary channels; and $\gamma_m$ is the maximum detector angle in $\gamma$.

\* \* \* \* \*